(12) United States Patent
Kerpelman et al.

(10) Patent No.: US 7,050,984 B1
(45) Date of Patent: May 23, 2006

(54) INTEGRATED INTERACTIVE SERVICE TO A PLURALITY OF MEDICAL DIAGNOSTIC SYSTEMS

(75) Inventors: Daniel I. Kerpelman, Whitefish Bay, WI (US); Richard L. Frowein, Waukesha, WI (US); Hubert Anthony Zettel, Waukesha, WI (US); James F. Kohli, Waukesha, WI (US); John Heinen, Wauwatosa, WI (US)

(73) Assignee: GE Medical Systems, Inc., Pewaukee, WI (US)

( * ) Notice: Subject to any disclaimer, the term of this patent is extended or adjusted under 35 U.S.C. 154(b) by 780 days.

(21) Appl. No.: 09/470,554

(22) Filed: Dec. 22, 1999

(51) Int. Cl.
*G06F 17/60* (2006.01)

(52) U.S. Cl. .............................. 705/2; 705/3; 600/300

(58) Field of Classification Search ................ 705/2–3; 345/733; 600/300
See application file for complete search history.

(56) References Cited

U.S. PATENT DOCUMENTS

| | | | |
|---|---|---|---|
| 4,982,325 A * | 1/1991 | Tignor et al. ................ 710/305 |
| 5,586,262 A * | 12/1996 | Komatsu et al. ................ 705/2 |
| 5,867,821 A * | 2/1999 | Ballantyne et al. ............. 705/2 |
| 6,006,191 A * | 12/1999 | DiRienzo ........................ 705/2 |
| 6,260,021 B1 * | 7/2001 | Wong et al. ..................... 705/2 |
| 6,272,469 B1 * | 8/2001 | Koritzinsky et al. ........... 705/2 |
| 6,353,445 B1 * | 3/2002 | Babula et al. ............... 345/733 |

FOREIGN PATENT DOCUMENTS

EP 833266 A2 * 4/1998

OTHER PUBLICATIONS

Lisa Picarille, Jul., 1994, Medical imaging a slow operation: Majority of health-care field still grapping over basic technology issues, Computer Reseller News p. 67.*
O. Ratib, M.D., Ph.D, Mar. 12, 1997, From PACS to the World Wide Web; Health on the Net (HON) http:/www.hon.ch/Library/paper/ratib.*
Lisa Picarille, Medical imaging a slow operation: Majority of health-care field still grapping over basic technology issues, Jul. 11, 1994, Computer Reseller News, Issn: 0893-8377, p. 67.*

* cited by examiner

*Primary Examiner*—Joseph Thomas
*Assistant Examiner*—Robert W. Morgan
(74) *Attorney, Agent, or Firm*—Fletcher Yoder (57) ABSTRACT

A technique is provided for servicing a plurality of medical diagnostic systems remotely. The systems are coupled to an internal network of a medical institution or facility. A data communications control system serves to link the institution to a remote service provider via an external network. Service requests and data are generated at the systems or at the control system. The requests are then transmitted to the remote service provider via the control system, and responses to the requests are received by the control system for distribution to the diagnostic systems. The technique permits systems to be remotely serviced which may not be equipped for separate communication via external networks, reduces infrastructure and costs, and facilitates the coordination of service needs of the institution.

32 Claims, 7 Drawing Sheets

INTEGRATED INTERACTIVE SERVICE TO A PLURALITY OF MEDICAL DIAGNOSTIC SYSTEMS

FIELD OF THE INVENTION

The present invention relates generally to the field of medical diagnostic systems, and to servicing such systems through a remote service provider. More particularly, the invention relates to a technique for facilitating servicing of a number of medical diagnostic systems in an interactive manner via network connections between the systems and a remote service provider.

BACKGROUND OF THE INVENTION

Medical diagnostic facilities, including clinics, hospitals, outpatient institutions, and departments within these organizations often dispose of an array of diagnostic systems. By way of example, a clinic or hospital may include a variety of medical diagnostic imaging systems in a radiology department, or in several radiology departments. Clinics and outlying or satellite offices may include additional equipment, both stationary and mobile. Such imaging systems may typically including magnetic resonance imaging (MRI) systems, computed tomography (CT) systems, x-ray systems, ultrasound systems, positron emission tomography (PET) systems, and so forth. Additional diagnostic systems may include various types of monitors, electronic examination or diagnostic tools, and so forth.

Due to the extremely demanding schedules and to the relative complexity of such systems and equipment, facilities typically contract for their oversight and maintenance with outside service providers. In a traditional servicing approach, a field service engineer physically visits a facility and review the state of operation of the systems, noting any potential problems, and ordering any necessary servicing to maintain the equipment in good operating condition. Such field engineer visits are also useful for upgrading equipment, including both physical upgrades and software upgrades. The field engineer, or other specialized personnel, may also visit the facilities to provide training or to answer questions regarding the proper configuration and operation of the equipment.

While conventional field service engineer visits are extremely useful in addressing specific needs as they occur, the remote servicing of medical diagnostic systems has been streamlined by networking the systems to a remote service provider. In one known approach, for example, individual diagnostic systems may be connected via an open or proprietary network to a remote service provider. The connection may be established at the initiation of the diagnostic system, or by the service provider, via conventional network technologies. Data required for providing the service, analyzing potential or existing problems, and so forth, is transmitted via the network connection. Moreover, service requests, and feedback on such requests, may be similarly transmitted via the network.

Networked remote servicing of medical diagnostic systems has proven extremely effective and will gain increasing acceptance in the future. However, such techniques are not without drawbacks. For example, a very substantial user base exists of systems which are not equipped for connectivity to an external network. In general, current technologies include the use of various types of modems for two-way data communication. However, where no such modem or similar circuitry is provided, a system may simply be unable to transmit or receive data for remote servicing. Moreover, where subscribing systems do include modems or other communications interfaces, separate connections and data transmission sessions are typically required for each of the systems, due to their independent management and to the overall topology of the remote service data exchange.

Another drawback of existing remote servicing techniques for medical diagnostic systems is the relatively limited coordination between the servicing and the internal or external reporting and accounting functions. Where individual diagnostic systems contact or are contacted by a remote service provider, for example, the remote service provider typically maintains data logs and accounting records for reporting back to the institution or facility to summarize service or maintenance activities. However, the institution itself may not be capable of, or may not efficiently maintain such records due to the independent contacts between the medical diagnostic systems and the remote service provider.

There is a need, therefore, for an improved technique for rendering service via a remote service connection to medical diagnostic systems. There is a particular need for a technique which will provide interactive exchange of data, requests, reports, and so forth, while reducing the number of separate connections needed, as well as the overhead of infrastructure required to formulate and transmit the data.

SUMMARY OF THE INVENTION

The present invention provides a remote service technique for medical diagnostic systems designed to respond to these needs. The technique is particularly well suited to facilities including a large number of diagnostic systems, both mobile and stationary. The technique may be applied to facilities and institutions having single locations or departments, or to distributed or integrated facilities having satellite offices, disparate departments, and so forth. Moreover, the technique is well suited to institutions or departments in which multiple systems are networked or may be networked through an internal network, such as an Ethernet network for rapid data exchange within the institution.

In accordance with a presently preferred embodiment, service data requests, data exchanges, and the like may be formulated either directly at individual diagnostic systems, or at a control system linked to the systems via an internal network. The data requests, in a general sense, may include both requests for maintenance or servicing of the systems, requests for information, requests for documentation, requests for examination of protocols, requests for software upgrades, and so forth. Once the request is formulated, a data communications control system transmits the request to a remote service provider via an external network.

DETAILED DESCRIPTION OF THE INVENTION

Figure 1:
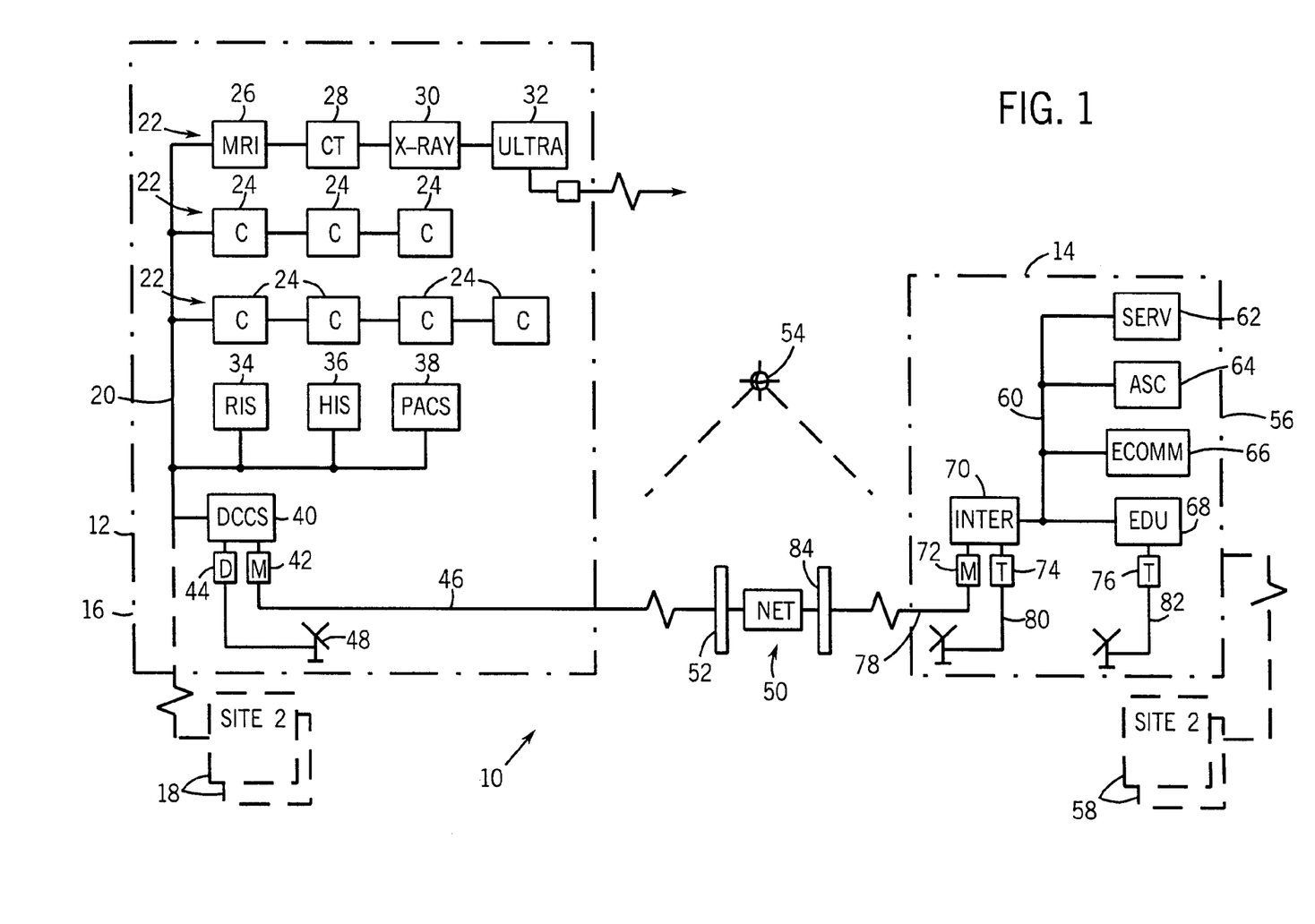
FIG. 1 is a diagrammatical overview of a data communications system for communicating data from a series of medical diagnostic systems to a remote service or data provider.

Turning now to the drawings, and referring first to FIG. 1, a data communications system, designated generally by the reference numeral 10, is illustrated for transmitting operational data or parameters from a series of medical diagnostic systems to a remote service or data provider. The system also permits interactive exchanges of data, service requests, software, and so forth between the systems and the remote service provider as described more fully below. As illustrated in FIG. 1, system 10 generally includes a medical diagnostic facility 12 which is linked to a remote service or data provider 14. The facility 12 may include a single location or site 16, or additional cites 18, which may be geographically local to or remote from site 16. In such cases, the additional sites may generally be interconnected with site 16 via a facility network.

Within facility 12, an internal network 20 provides a mechanism for data communications between a series of medical diagnostic systems, which where desired may be provided in groups or departments 22, such as floors, wards, specialized treatment or diagnostic areas, and so forth. A series of medical diagnostic systems, referred to herein generally as clients 24, are coupled to network 20 either through permanent network connections, or through temporary network connections. Thus, while some or most of the clients 24 may be stationary, certain of the clients may be mobile, allowing the client or asset to be utilized in a desired location, and to be coupled to the internal network once positioned at the desired location.

As used herein, the term medical diagnostic system should be understood to include a wide variety of equipment, systems and subsystems. By way of example, medical diagnostic systems may include diagnostic imaging systems designed to produce useful images of patient anatomies in accordance with particular physics or modalities. Other medical diagnostic systems may include patient monitors, sensors, transducers, and other signal-generating or feedback devices. Moreover, the medical diagnostic systems communicating in accordance with the present technique may include information management systems, workstations, image and data viewing stations, and so forth.

By way of example, in FIG. 1, a series of medical diagnostic imaging systems are illustrated in one group. In practice, this group may be physically or logically associated with a radiology department or clinic. In the embodiment illustrated in FIG. 1, these systems include a magnetic resonance imaging (MRI) system 26, a computed tomography (CT) system 28, an x-ray system 30, and an ultrasound system 32. These systems all preferably comprise client diagnostic systems for the present technique. As will be appreciated by those skilled in the art, each of these imaging systems is configured to produce useful image data based upon particular physics of their respective modality. As noted above, certain of these systems may be mobile, such as ultrasound systems which may be relocated to a desired room or examination area and connected to network 20 at that area or upon return to a base station.

By way of further example, in the embodiment illustrated in FIG. 1, the client diagnostic systems also include a series of data management stations. As indicated by reference numeral 34, then, the clients may include a radiology department informational system (RIS) designed to manage the production and flow of image data in conjunction with imaging systems 26, 28, 30 and 32. A hospital information system (HIS) 36 provides additional data, patient, financial, and other support for the operation of facility 12 in accordance with generally known techniques. Finally, a picture archiving and communication system (PACS) 38 provides for storage, processing, access and archiving of data files produced by the diagnostic imaging systems.

Each of the client diagnostic systems is coupled to network 20 for exchanging data with a remote service or data provider as described below. In heretofore known data exchange techniques, certain of the client systems may be equipped for independent exchange of operational or parameter data as required for servicing, maintenance, analysis, accounting and similar needs. In accordance with such techniques, an independent connection could be established between the assets and a remote service provider, such as via an independent modem connection as illustrated for ultrasound system 32 in FIG. 1. In accordance with the present technique, although certain of the systems may continue to permit such direct connection, the client diagnostic systems need not be capable of such separate connectivity. Rather, data may be exchanged between the systems and a remote service or data provider via network 20.

In the presently preferred embodiment, network 20 comprises a high-speed internal network, such as an Ethernet network. In current embodiments, the network may be a 10 Mb or a 100 Mb network exchanging data in accordance with a standard data exchange protocol, such as TCP/IP. Of course, other internal network architecture and standards may be employed.

The communications system further includes a data communications control system (DCCS) 40 which is coupled to network 20 for receiving or accessing data from the client, and for exchanging data with one or more remote service or data providers. The DCCS 40 is thus coupled to external communications circuitry, such as a modem 42 and a satellite decoder 44. Modem 42, and any additional modems as desired, may be of any suitable type, such as a 56 kb/s modem in accordance with present technology, a cable modem, or any suitable external network communications interface. Decoder 44 may similarly be any suitable satellite or wireless interface, such as an IRD of the type available from Scientific Atlanta of the United States. As described more fully below, the use of parallel media for transmitting and receiving data permits the DCCS 40 to optimize the use of available bandwidth in data exchanges between the facility and the remote service provider. By way of example, modem 42 may provide bandwidth of 56 kb/s, while decoder 44 offers a considerably broader bandwidth, such as 500 kb/s.

The data communications to and from facility 12 are provided by an external network link 46 routed to modem 42, and by a satellite link 48 routed to decoder 44. External network link 46 is coupled, such as via conventional telephony cables, optical fibers, or otherwise, to a network 50, such as a wide area network. Network 50 may be any suitable type of network, however, including virtual private networks, or the Internet. Isolation and protection of the integrity of the information system of facility 12 may be assured by one or more firewalls 52. Satellite link 48, which also generally forms part of the external network for communicating data to and from the facility, functions to receive data relayed via satellite 54, or through ground-based repeaters, transmitters, and so forth.

Data from facility 12 is exchanged with a service provider 14 through the external network connections described above. In general, remote service provider 14 may include a principle site 56, and additional cites 58, interconnected through open or proprietary networks. Remote service provider 14, by way of example, may include a facility or facilities for receiving data and service requests from the medical diagnostic facility on a subscription or contract basis. Services, data, training, technical assistance, and other information may then be provided to the subscribing facilities through the network connections and in accordance with the techniques described below. In the illustrated example, remote service provider 14 includes its own internal network, such as an Ethernet-based local area network.

A series of clients or systems are interconnected via the network for exchanging data both internally and with the medical diagnostic facility. By way of example, a service system, designated generally by reference numeral 62, is provided for receiving and processing service data, such as service requests, protocol requests, questions, and so forth. Service system 62 may also be equipped for scheduling regular or special service calls, providing reports and analysis of operational or parameter data, and so forth. In the illustrated example, remote service provider 14 also includes an automated support center as represented generally at reference numeral 64. The center may perform a variety of automated functions, including the acquisition or collection of operational parameters and data from the facility as described below. In general, many or all of the functions performed by the ASC may be fully automated, requiring little or no operator intervention. Data collected in accordance with the routines executed by the ASC are stored and made available upon demand. Remote service provider 14 may also include various electronic commerce systems 66 designed to provide data, receive orders, process orders, and perform accounting and financial transactions upon request from the medical diagnostic facility. An educational unit or system 68 may further be provided for offering educational or training programs, providing manuals or documentation, and so forth.

While certain of the systems of the remote service provider may be configured for direct link to one or more medical diagnostic facilities or diagnostic systems, in the illustrated example, they are configured for communication with the diagnostic systems over the internal network 60 and through a communications interface 70. Communications interface 70 will typically include a data router, and other hardware and software for appropriately addressing data received from the medical diagnostic facility to one or more of the internal systems of the remote service provider, and for directing communications from these systems to the medical diagnostic facility. Interface 70 communicates the data via one or more modems 72, and via a satellite transmitter 74. Where desired, further network or satellite links may be provided to specific systems of the remote service provider such as a transmitter 76 provided for the educational unit 68. Each of the communications devices is coupled to a data link, including a fresh data link 78 for modem 72, and satellite links 80 and 82 for transmitters 74 and 76, respectively. The data link 78 preferably protects the integrity of the network and data of remote service provider 14 via one or more firewalls 84 or similar protection devices.

The system topology illustrated in FIG. 1 permits data to be exchanged interactively between the medical facility and the remote service provider. As discussed below, the data may be exchanged at the initiation of the medical diagnostic facility, or of systems within the facility, via DCCS 40. Alternatively, communications may be initiated by the remote service provider, such as to respond to data or service requests, to access or acquire data from the diagnostic systems through the DCCS, or to provide various services, including instructional materials, training sessions, and so forth, via the external network links.

Figure 2:
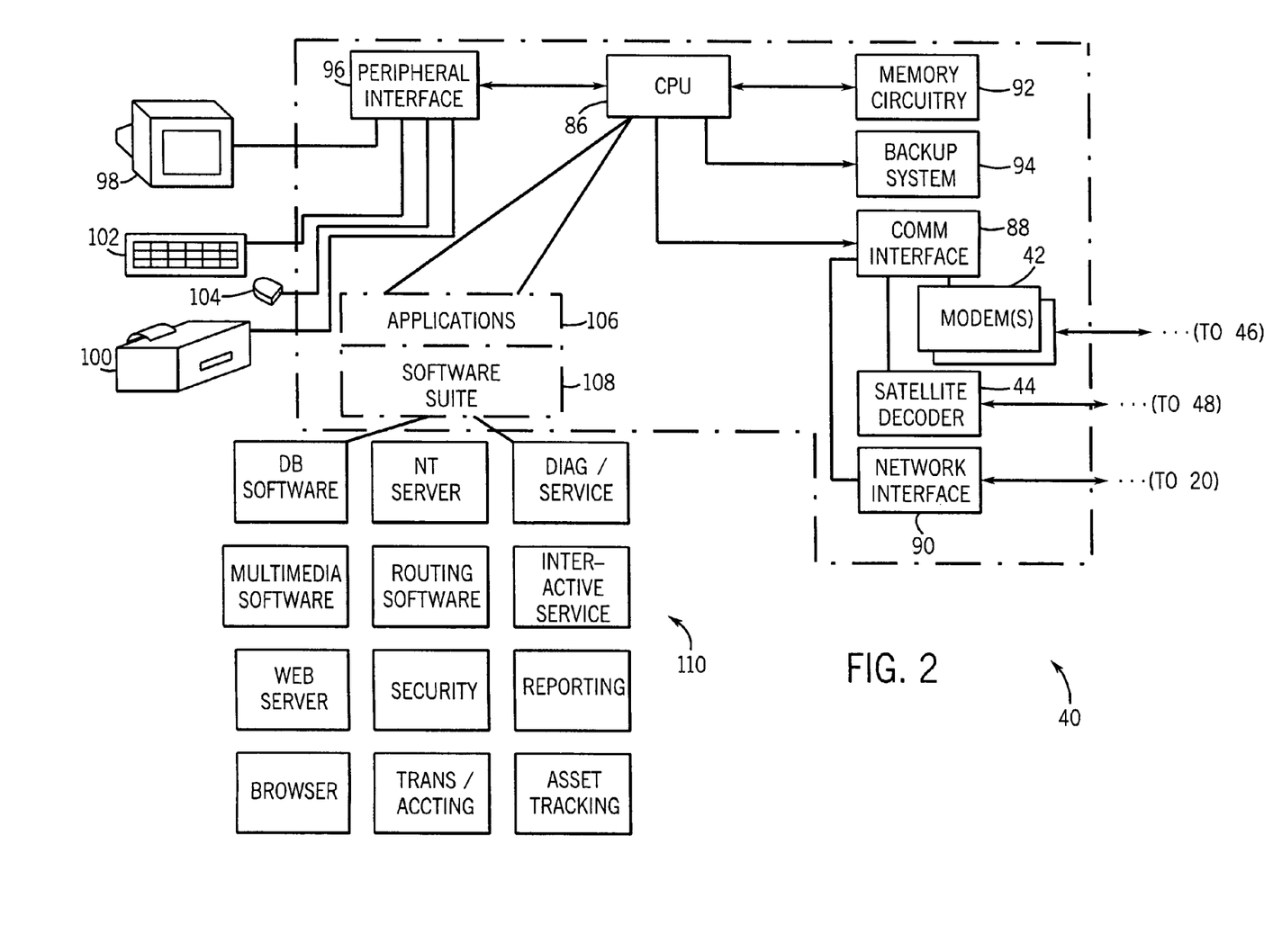
FIG. 2 is a diagrammatical view of an exemplary data communications control system in accordance with certain aspects of the present technique for use in the system shown in FIG. 1.

FIG. 2 illustrates an exemplary configuration for DCCS 40, including its associated peripheral devices and software suite. In the illustrated embodiment, DCCS 40 includes a central processing unit 86, which may comprise a commercially available microprocessor within a general purpose or application-specific computer. The CPU is coupled to a variety of hardware and functional circuitry to carry out the functions described herein. For example, as shown in FIG. 2, the CPU is coupled to a communications interface 88 to transmit and receive data via the external network as described above, and to similarly transmit and receive data with the diagnostic systems via the internal network. Thus, communications interface 88 may coordinate communications through one or more modems 42 coupled to the data link 46. The satellite decoder 44 similarly channels data through the DCCS via satellite link 48. An additional network interface 90, such as an Ethernet interface, permits the exchange of data via the internal network 20 of the facility.

In addition to these communication components, DCCS 40 includes memory circuitry 92 and additional support components. Memory circuitry 92 may include any suitable memory, such as disc drives, random access memory, read-only memory, dynamic random access memory, optical storage, and so forth. Memory circuitry 92 stores both software routines executed by the DCCS, as well as data collected by the DCCS for transmission to the remote service provider, and data received from the remote service provider for distribution to designated or addressed diagnostic systems of the facility. A backup system 94 is preferably provided for periodically creating archive versions of selected files, routines, collected data, and so forth. One or more peripheral interfaces, as designated generally at reference numeral 96, is provided for receiving input signals from an operator interface, and for displaying data and outputting data as desired. In the illustrated embodiment, such peripheral devices include a computer monitor 98 and printer 100 as output peripherals. Input peripherals may include a conventional keyboard 102, mouse 104, and any other suitable input peripheral devices.

While certain software applications and utilities may be stored and executed on various clients of the facility, particularly within the imaging systems, the RIS, the HIS, and the PACS, DCCS 40 preferably independently executes a variety of applications to perform the data communications functions assigned to it. These applications, designated generally by reference numeral 106 in FIG. 2, are preferably stored in memory circuitry 92, and executed by CPU 86. Alternatively, certain of the applications may be resident elsewhere, and completely or partially executed by other data processing circuitry. The applications 106 will generally include a variety of commercially available application routines, and may further include customized routines executed by the CPU. A software suite 108 is therefore available for execution by the CPU, both automatically, on a regularly scheduled basis, or in response to operator prompts or prompts from the remote service provider.

Application routines, designated generally by reference numeral 110 in FIG. 2, may include software for collecting data from the diagnostic systems, storing such data, transmitting data to the remote service provider, and routing data from the service provider to designated systems. In the embodiment illustrated in FIG. 2, software suite 108 includes database software for associating collected data from the diagnostic systems in a relational manner. Such data preferably includes the identification of the systems, their locations, utilization data, as well as a variety of parameter data useful in determining the operational state of the system and the possible need for service. As will be appreciated by those skilled in the art, in the case of diagnostic imaging systems, a wide variety of operational or parameter data may be stored directly at the individual diagnostic systems and may provide extremely useful indications of the performance of the systems, and possible future service needs.

Software suite 108 preferably also includes server software, such as Windows NT server software from Microsoft Corporation of Redmond, Wash., as well as web server software. The server software permits the DCCS to function as a server, both for the internal clients and for external clients or users. Browser software is also preferably included, permitting an operator, through the operator interface devices of the DCCS, to log on to sites, such as on the Internet to request information and data, transmit service and data requests, and so forth. In the preferred embodiment, the browser software may also function on the DCCS to permit interactive interfacing directly at one or more of the diagnostic systems, particularly the diagnostic imaging systems. Routing software is also functional on the DCCS to permit data packets received from the remote service provider to be appropriately transmitted to designated diagnostic systems within the facility via the internal network.

Additional applications of software routines are also preferably included on the DCCS, including diagnostic and service routines, and interactive service routines. These routines, which may include an interactive service platform, permit service requests to be generated, preferably via a web browser interface for immediate of delayed transmission to the remote service provider. These applications also preferably permit the receipt of reports and service data back from the remote service provider in an interactive fashion. Reporting software on the DCCS permits reports to be generated, particularly reports relating to communications activities logged as described below. Security routines may be executed as part of the software suite, preferably to verify the integrity of data transmitted and received via the DCCS, and to limit access both to the internal network from outside users, including the remote service provider, and access to remote websites or providers from the clients coupled to the internal network.

Asset management applications preferably also run on the DCCS to enable various business, financial, and management functions to be performed, preferably in coordination with similar functions performed by the RIS and HIS. In the illustrated embodiment, for example, transactional and accounting routines may be operational, such as to maintain an accounting for remote services utilized by the facility, any charges or fees associated with such services, similar accounting for any electronic commerce transactions performed, and so forth. An asset tracking routine may provide for analysis of locations and availability of specific clients or assets, particularly of mobile clients which may be traced through the internal network to specific locations.

The components of the software suite illustrated in FIG. 2 and discussed above, may include various commercially available applications software packages, or software which is created specifically for the facility or application. In general, however, any application-specific software may be readily developed by those skilled in the art, without undue experimentation. In the presently preferred embodiment, commercially available software applications included in the system and executed by the DCCS include database software available from Oracle Corporation of Redwood City, Calif., multimedia software available from Eloquent Systems, Inc. of North Vancouver, British Columbia, web server software, such as Netscape Enterprise software available from Netscape Communications of Mountain View, Calif., and browser software, such as software available from Microsoft Corporation of Redmond, Wash., or Netscape Communications.

Figure 3:
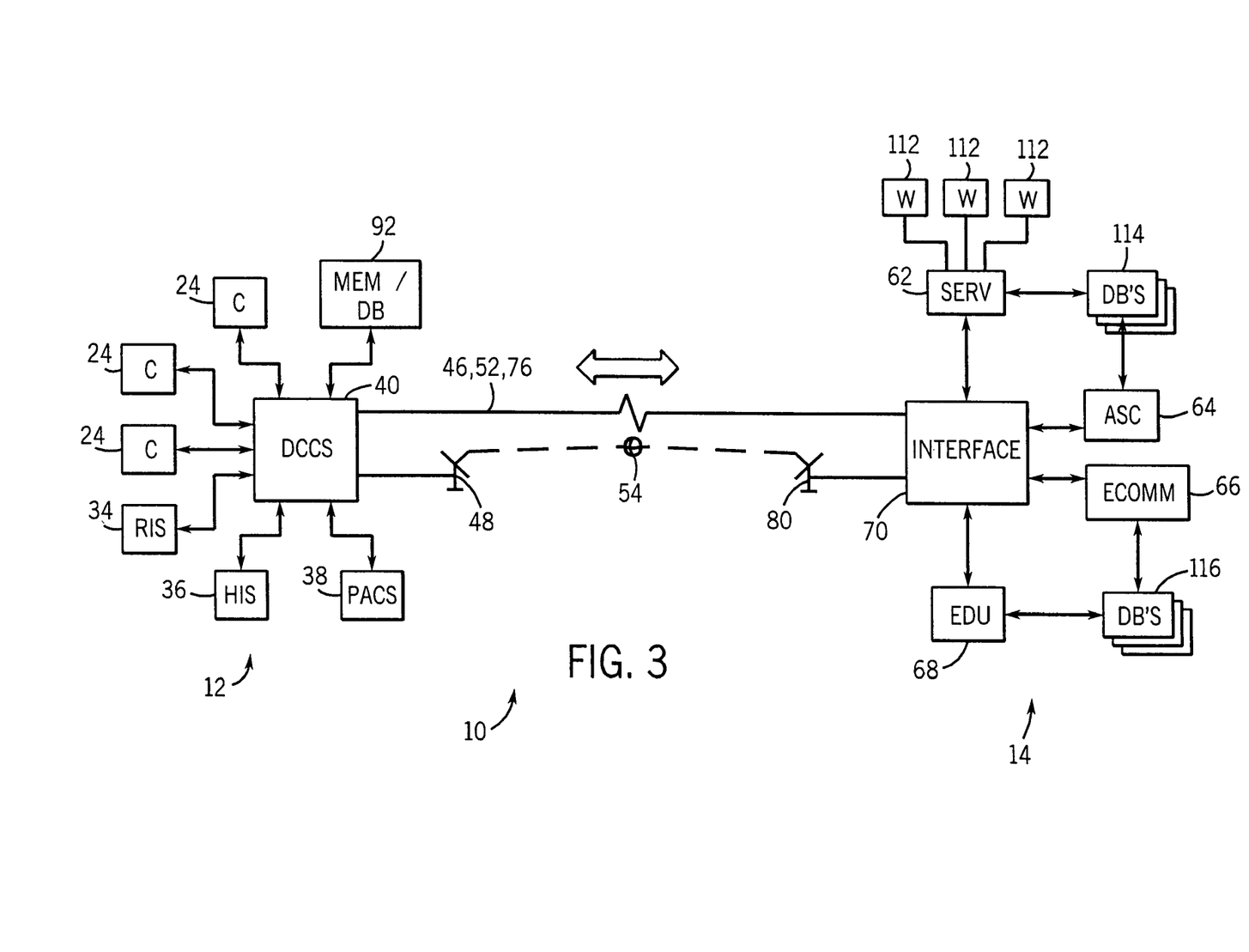
FIG. 3 is a data flow diagram illustrating the paths that data takes in the communications through the various components of the system of FIG. 1.

FIG. 3 illustrates general flow of data within the overall system topology illustrated in FIG. 1. As shown in FIG. 3, two-way data flow is provided between the DCCS 40 and the various clients 24, and other networked systems, such as the RIS 34, the HIS 36, and the PACS 38. As noted above, clients 24 preferably include medical diagnostic imaging systems which are linked to the remote service provider through the DCCS for interactive data and service needs. DCCS 40 also communicates data to and from memory circuit 92, which in the diagram of FIG. 3 may include databases, both local to the DCCS and at various networked nodes of the facility.

Within remote service provider 14, data may be exchanged between interface 70 and the various systems and subsystems, such as those described above, as service system 62, ACS 64, electronic commerce systems 66, and educational units or systems 68. Each of these systems may include other networked systems or stations, such as work stations 112 which, through the service system 62 permit applications engineers to access diagnostic system data, address specific service needs and requests, and so forth. One or more databases 114 and 116 are preferably linked to the systems of the remote service provider to permit parameter and operational data to be stored relationally, and retrieved as desired for analysis, reporting, invoicing, and so forth. It should be noted that the components of the remote service provider, including the systems illustrated in FIG. 3, may exchange data either locally or through a wide variety of network configurations, including configurations permitting one or more of the systems and databases to be located in geographically distant locations from one another.

The data exchanged internally within the medical diagnostic facility and the remote service provider are then exchanged via the external network links between these facilities. In the illustrated embodiment, these network links include the satellite links 48 and 80, routing data through a satellite 54 or land-based circuitry, as well as a wide area network as defined by links 46 and 78, and network 50.

The data communications technique and components described above permit access to and exchange of data in accordance with a variety of routines. Logical steps in certain of these routines are illustrated in FIGS. 4–9.

Figure 4:
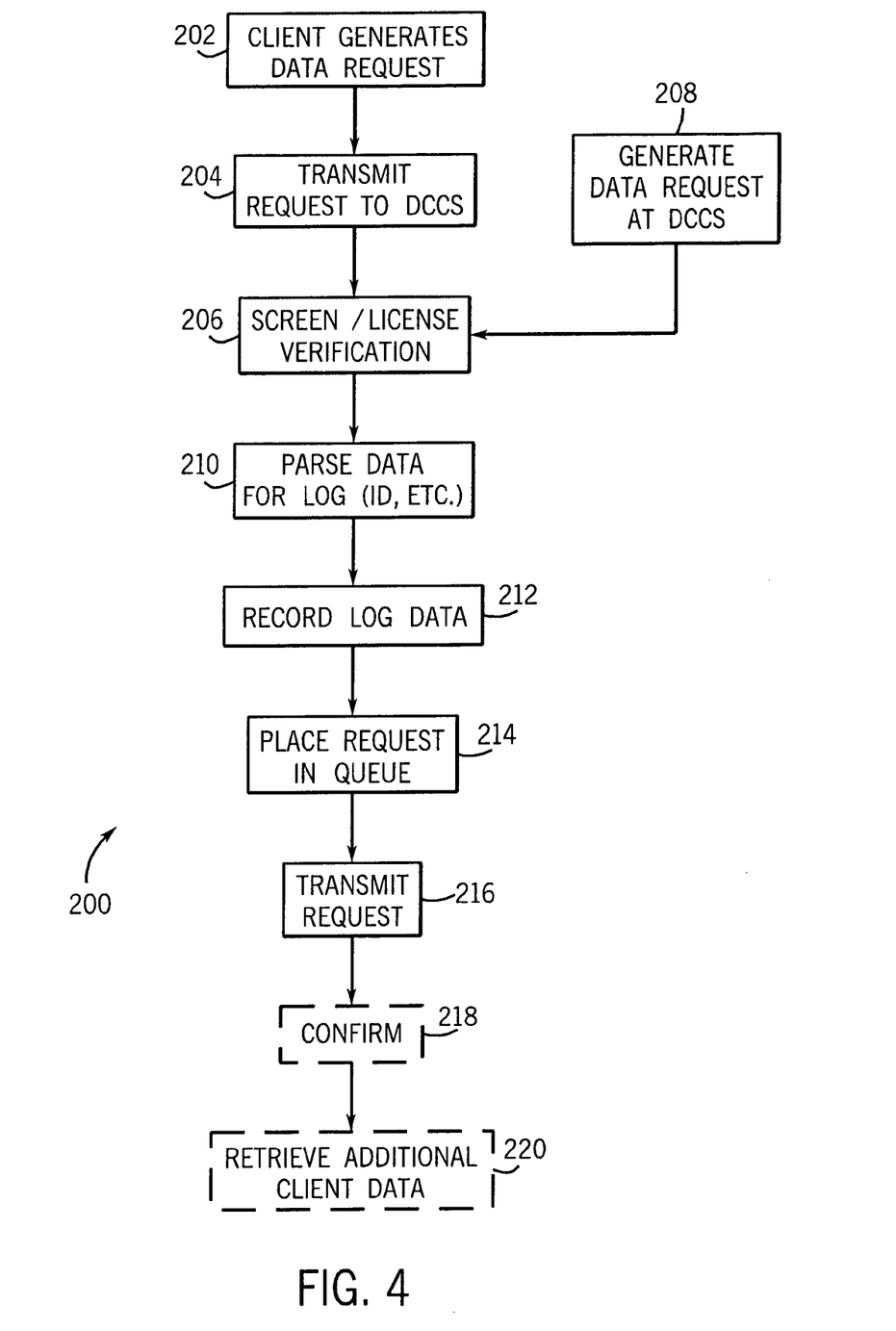
FIG. 4 is a flow chart illustrating exemplary control logic in initiating a service request or other data transfer between a medical diagnostic system and a remote service provider.

Referring to FIG. 4, a first routine permits service and data requests to be formulated at the diagnostic facility for transmission to the remote service provider. The service request routine, designated generally by reference numeral 200, begins at step 202 where a client of the facility generates a data request. In the present context, such data requests may include a wide range of service, data, software, and similar requests. Specifically, for medical diagnostic imaging systems, these requests may include descriptions of specific problems occurring at the system, requests for imaging protocols for software, operational inquiries, and so forth. However, similar requests may originate in networked clients, such as internal training services of the facility, such as for multimedia training materials which may be transmitted through the DCCS as described below. It should also be noted that the data request may be formulated at diagnostic systems which include software running locally for the request formulation, or through applications running on the DCCS and accessible through the diagnostic system. At step 204, these requests are transmitted to the DCCS. At step 206, the requests are screened and any license verification may be performed, such as to determine whether the requesting diagnostic system is currently licensed for the type of request made.

As indicated at step 208 in FIG. 4, service or data requests may be generated directly at the DCCS 40. Such requests may be formulated through the operator interface components of the DCCS, preferably through an interactive interface, such as a web browser or other graphical user interface. It should be noted that the ability to generate data and service requests directly at the DCCS offers significant advantages over existing techniques for interactive service of diagnostic systems. For example, where the installed base of equipment in a medical facility is not or cannot be equipped for direct communication via an external network, the equipment can nevertheless be coupled to the DCCS via the internal network. Moreover, many medical diagnostic systems and devices are not equipped for operator interface so as to permit formulation of service and data requests. However, the ability to generate such requests directly at the DCCS allows such systems to be included in an overall service provision scheme. Following generation of the request at step 208, the screening and license verification functions of step 206 may be performed as indicated in FIG. 4.

At step 210 in FIG. 4, the data included in the request is parsed, such as to identify the requesting or designated diagnostic system, specific problems or issues to be addressed, an operator or clinician formulating the request, and so forth. At step 212, this information is logged in the memory circuitry of the DCCS. At step 214 the request is placed in a cue for transmission to the remote service provider. Where a connection session is currently taking place, the request may be transmitted at the earliest communications window available, as indicated at step 216. Where necessary, transmission at step 216 may require the initiation of a connection session. In the presently preferred embodiment, such connections may be initiated either by the DCCS, or by the remote service provider. Where desired, receipt and transmission of the request is confirmed back to the designated diagnostic system as indicated at step 218.

Moreover, where additional client data is necessary to address the request, this data may be retrieved as indicated at step 220. Such data may include particular configurations or parameter settings which may have been in place during an imaging sequence, for example, data streams produced by an imaging system or monitor, service history data, and so forth.

Figure 5:
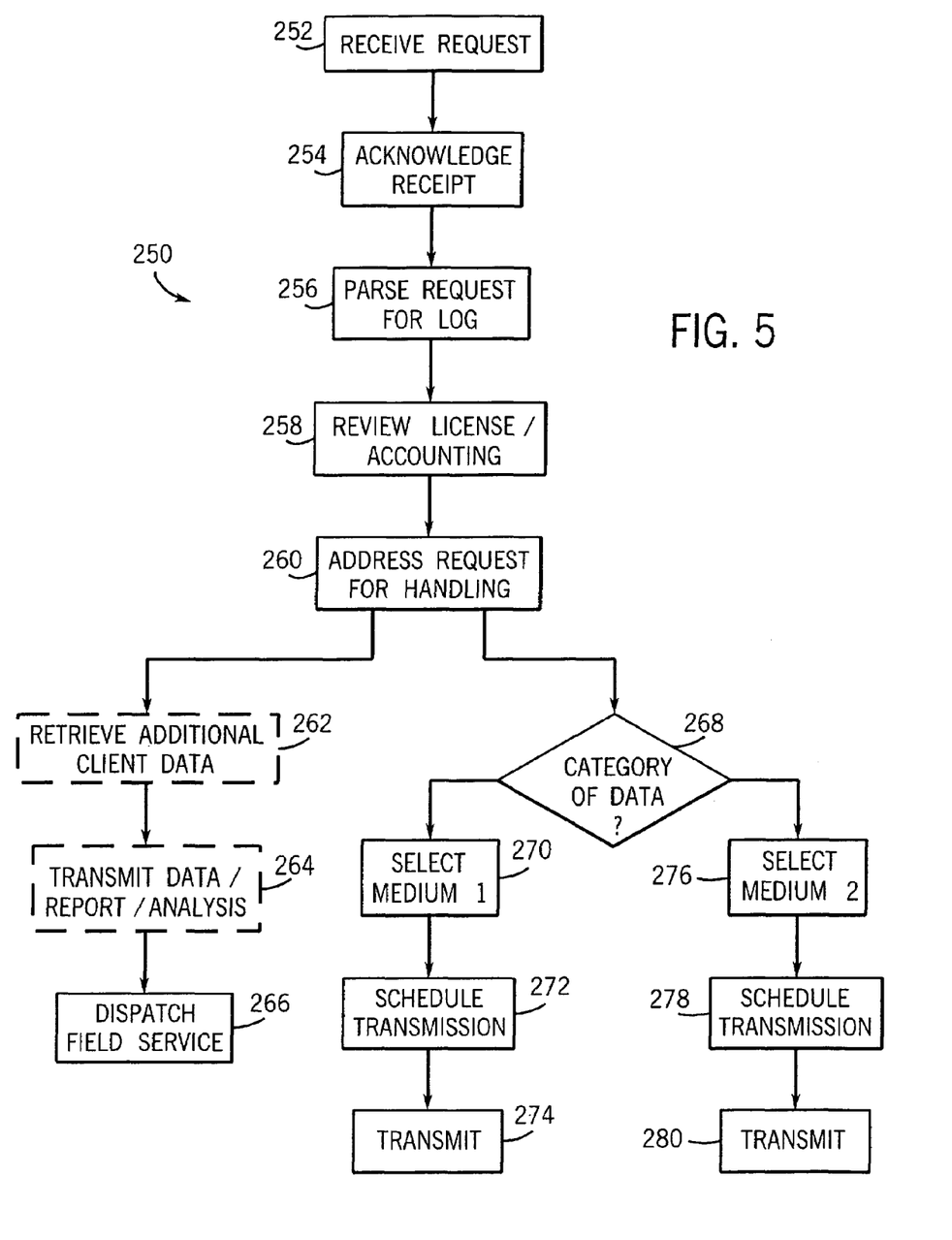
FIG. 5 is a flow chart illustrating exemplary control logic in handling service or data requests by a remote service provider, and for retransmitting data in response to such a request.

The requests formulated in accordance with the logic of FIG. 4 are transmitted via the external network to the remote service provider. FIG. 5 illustrates exemplary logical steps in handling such requests. The handling procedure, indicated generally by reference numeral 250, begins with receipt of the request at step 252. At step 254 an acknowledgment message may be formulated by the remote service provider, such as through an automatic return messaging routine, and sent back to the DCCS for informing the facility that the request has been received and is being handled. Such acknowledgement may include additional details regarding the handling, such as reference numbers, dispatch numbers, handling schedules, and so forth. At step 256, data from the request is parsed for logging by the remote service provider. The parsing performed at step 256 may include parsing for similar data to that reviewed at step 210 of FIG. 4, such as for an identification of the requesting or designated system, identification of the facility, service subscription data, and parameter or operational data necessary for reviewing and addressing the request. At step 254, license or accounting records stored within a database of the remote service provider are accessed and updated to make note of the request. Depending upon the desired accounting structure, the request may be handled under an existing contract or subscription, on a warranty basis, on a pay-per-use basis, or otherwise.

As noted above, depending upon the type of request transmitted from thee medical diagnostic facility, its handling by the remote service provider may assume various modes. As indicated at step 260 of FIG. 5, the request is addressed within the service provider for handling, such as for automatic handling, or for intervention of a service engineer. In either event, it may be necessary to obtain additional data from the system to properly address the service request. In the case of medical diagnostic imaging equipment, such additional information may include raw or processed image data files, system configuration parameters and settings, and so forth. As indicated at step 262, such data may be retrieved through the external network, DCCS, and internal network of the facility. Once sufficient information has been accessed to address the request, the requested data, reports, analysis, and so forth may be then transmitted from the remote service provider back to the designated medical diagnostic system through the DCCS, or directly back to the DCCS where the request originated there. The transmissions at step 264 may include a wide range of data. For example, the data may include configuration parameters, suggested troubleshooting steps, electronic messages, electronic documentation, software upgrades, protocols, and so forth. Where necessary, a field service engineer may be dispatched, as indicated at step 266 in FIG. 5 for additional follow up. The field service engineer dispatched at step 266 may address the request either in person or remotely, such as through telephone or other connections from the remote service provider.

As noted above, responses to requests from the medical diagnostic facility may be transmitted through alternative media, such as a wide area network and a satellite link. The logic of FIG. 5 illustrates one embodiment for processing such transmissions in response to requests. While various media may be employed for this purpose, in a presently preferred embodiment the media have significantly different transmission rates or bandwidths, enabling certain types of transmissions to be made through a first type of connection, such as the wide area network, with more demanding or specific transmissions being made through a higher bandwidth medium. Various approaches may be adopted for deciding which of the media will be employed for the transmission. For example, the remote service provider may manually or automatically select a media depending upon the requirements or preferences of the medical diagnostic facility. Moreover, specific types of transmissions may be made over one medium or the other, such as streaming media transmissions which may require substantial bandwidth, may occupy a link for substantial periods of time, or may be particularly susceptible to interruption or network delays.

In the presently preferred embodiment, the selection of the wide area network or the satellite link is made based upon a category of data or transmission. Thus, at step 268 of FIG. 5, the category is reviewed and one of the available media is selected. By way of example, multi-media presentations, training sessions, and similar data categories are transmitted through the satellite link, while more conventional data transmissions are made through the wide area network. Depending upon the transmission category, then, the medium is selected as indicated at either step 270 or 276. The transmission is then scheduled as indicated at step 272 or step 278. In the case of training sessions, for example, the transmission may be scheduled for a later date and time, with the designated diagnostic system being a specific location, training room, or other client of the diagnostic facility. Finally, as indicated at either step 274 or 280, the scheduled transmission is made through the selected medium.

Figure 6:
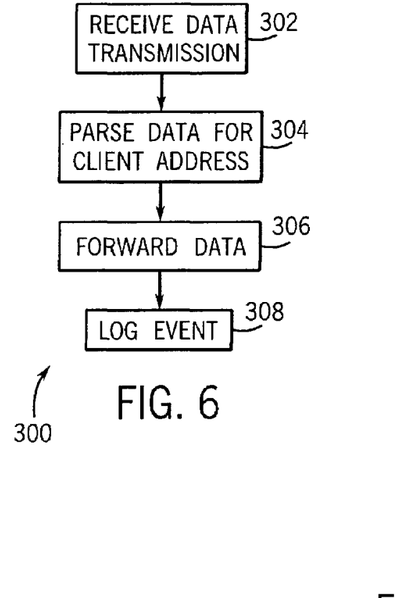
FIG. 6 is a flow chart illustrating exemplary control logic for receiving a transmission from a remote service provider at the medical diagnostic facility.
Figure 7:
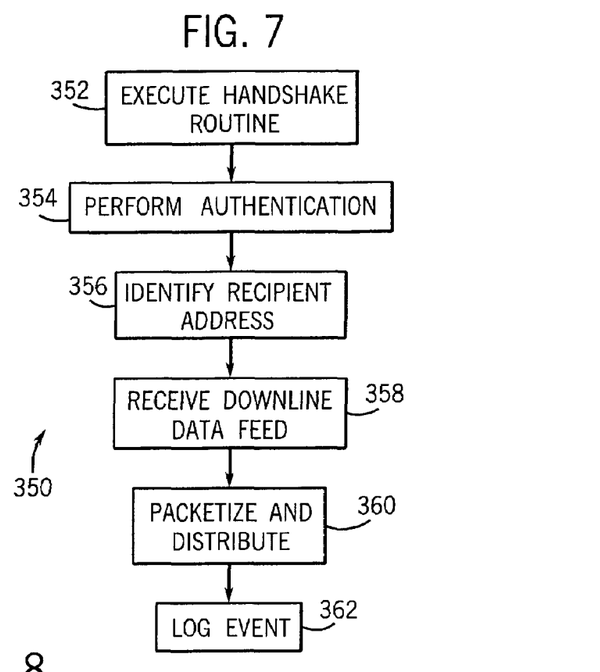
FIG. 7 is a flow chart illustrating exemplary control logic for receiving data via an alternative data communications medium.

FIG. 6 indicates exemplary control logic for receiving and processing transmissions back from the remote service provider to the diagnostic facility. This control logic, designated generally by reference numeral 300, begins with receipt of the data transmission at step 302. This receipt is through the DCCS, such as in an ongoing data transmission session. At step 304, the data received is parsed to identify at least the designated or addressed diagnostic system. At step 306 the data is forwarded from the DCCS to the designated system via the internal network of the facility. It should be noted that step 306 may include storing all or part of the data, or information derived or parsed from the data in the memory circuitry of the DCCS, or in another database of the facility. At step 308 the receipt and communications exchange is logged by the DCCS.

Where required, alternative procedures for the receipt and processing of data may be implemented as indicated in FIG. 7. The alternative receipt steps indicated generally by reference numeral 350, may be desirable, for example, in the receipt of digital data via satellite links, with the data being routed through the DCCS for distribution. In particular, such satellite communications systems, or other alternative media, may not require two-way communication. Accordingly, certain of the information for addressing the data may be transmitted in parallel through the other medium, particularly through a wide area network. Thus, at step 352, a handshake routine is executed between the DCCS and the remote service provider to insure appropriate connectivity and the ability to exchange the necessary information. At step 354, an authentication procedure may be performed to insure that the transmission session via the parallel medium conforms to the request and to the transmission schedule. At step 356, the recipient address is identified and confirm, such as to insure that the transmission channel is appropriately tuned or selected, and that the client or diagnostic system is identified within the facility. At step 358, the transmission is received and demodulated, filtered, or otherwise processed. As indicated at step 360, the data received via the parallel medium may require additional processing, such as to packetize the data for transmission over the internal network. Following such processing, the data is distributed to the designated system. The communication sequence and transmission is logged as indicated at step 362.

Figure 8:
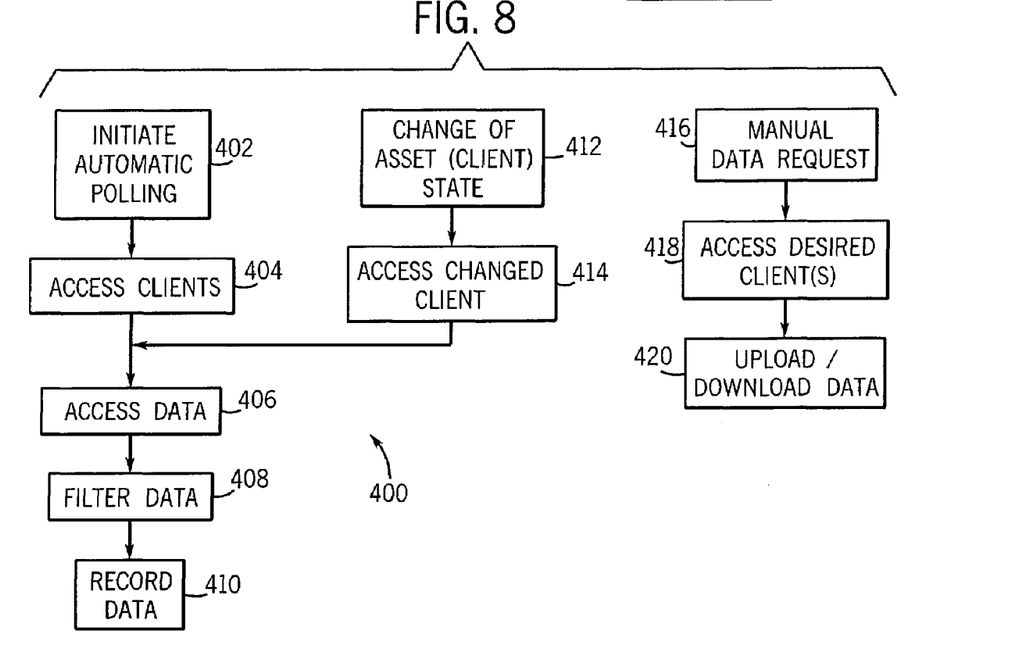
FIG. 8 is a flow chart illustrating exemplary control logic in polling or sweeping systems of a medical diagnostic facility or data for retransmission to a remote service provider.

In addition to the interactive exchange of service and other data, the present technique permits the acquisition of operational and parameter data from the medical diagnostic systems which are clients of the internal network of the facility via a streamlined procedure. FIG. 8 illustrates exemplary steps in this procedure, through control logic designated generally by reference numeral 400. In general, the procedure enables the data to be acquired or collected from the networked diagnostic systems through the DCCS, and transmitted from the DCCS to the remote service provider. In heretofore known approaches to providing service to medical diagnostic systems, such data was typically acquired through direct connection to a desired diagnostic system, requiring a large number of connections to be made independently and placing substantial demands on infrastructure, both within the facility and at the remote service provider. Moreover, where diagnostic systems were not equipped for connectivity directly to the remote service provider, little or no information could be obtained, particularly directly from the system.

In the present approach, information may be obtained through several different processes, initiated both automatically and manually. In the exemplary logic of FIG. 8, the data acquisition process may begin with initiation of an automatic polling routine at step 402. This routine would be executed by the DCCS which contacts each networked system, or designated systems from which data is desired, on a preestablished schedule. By way of example, the schedule may include periodic data acquisition throughout a 24 hour period, or less frequent acquisition. Depending upon the routine and schedule, the clients are contacted at step 404 of FIG. 8. At step 406 the data is accessed, such as by retrieval from memory circuitry of the client diagnostic systems. At step 408 the data may be filtered, such as to determine whether complete or incomplete information is acquired, to parse data which is not desired, such as patient-specific data, and so forth. At step 410, the data is recorded, such as in the memory circuitry of the DCCS.

As an alternative to the polling process described above, certain data may be collected upon occurrence of a specific event in the diagnostic system or within the facility. For example, where certain of the systems of the facility are mobile, connection of the mobile system to the internal network may cause the DCCS to execute the data acquisition routine for the newly-connected system. Thus, as indicated at step 412 of FIG. 8, the specific system or asset may change a state, such as establishing or renewing a connection to the internal network. At step 414, then, the system is accessed and desired information is transferred from the system to the DCCS. By way of example, to permit asset tracking, asset management, productivity analysis, and other functions, the location of mobile assets may identified and recorded for later use, or to permit the facility personnel to track the assets.

The data acquisition sequences may also be initiated by a manual request, as indicated at step 416 in FIG. 8. The manual request may be input via the operator interface components of the DCCS, such as to access and display performance, utilization, and other characteristics or parameters of the networked systems. In response to the manual request, the designated system is accessed, as indicated at step 418, and the desired data is located and transmitted from the device memory as indicated at step 420.

Figure 9:
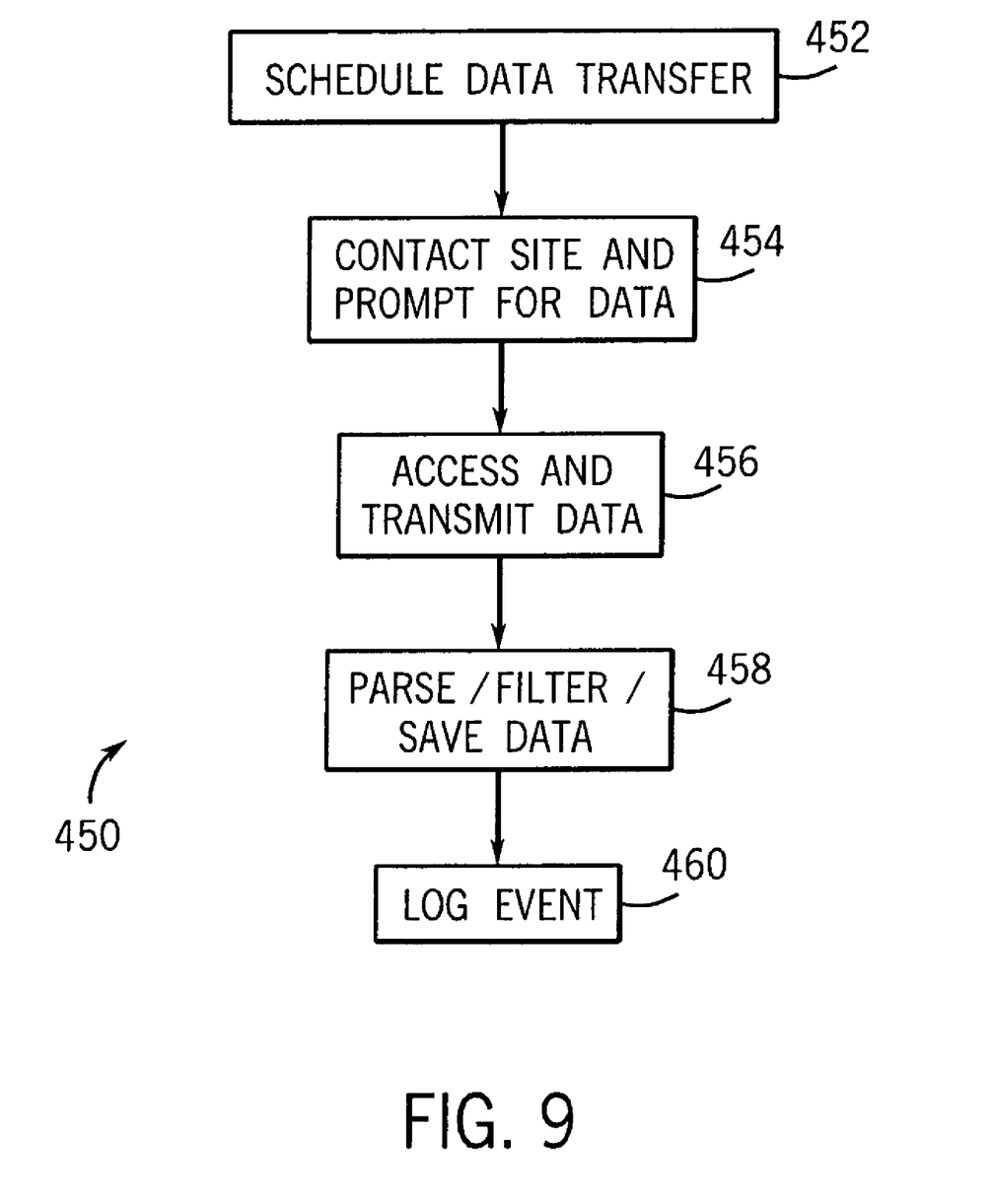
FIG. 9 is a flow chart illustrating exemplary control logic for accessing the data collected in the process of FIG. 8 for handling and storage by a remote service provider.

To facilitate transmission of acquired data to the remote service provider, the acquired data is preferably stored locally at the diagnostic facility, and transmitted to the remote service provider in one or more data communication sessions. Such sessions may be scheduled for convenient times, such as during off-peak hours, nighttime hours, weekends, and so forth. FIG. 9 illustrates steps in exemplary control logic, designated generally by reference numeral 450, for transmitting the data once acquired at the facility.

Referring to FIG. 9, the data transfer is first scheduled as indicated at step 452. As noted, this schedule may be established for convenient times, both for the diagnostic facility and for the remote service provider. It should be noted, however, that such data transfers may be initiated by operator intervention, where desired. As indicated at step 454, a connection is then established between the diagnostic facility and the remote service provider. The connection may be initiated by either the facility or the remote service provider, the remote service provider being the preferred initiator in the present embodiment. Also, at step 454, the remote service provider prompts the transfer of the data, such as through a communications routine stored at both the DCCS and the remote service provider. In response to the prompt, the data is accessed from the medical facility memory or data repository and transferred to the remote service provider as indicated at step 456. During or following the transfer, any desired parsing, filtering, and other processing are performed as indicated at step 458. In particular, the transferred data is preferably parsed to identify the individual diagnostic systems originating the data, and to separate operational and parameter data for the individual systems from one another. The data is then stored, preferably in relational databases, for later retrieval and analysis. Finally, at step 460, the data transfer session is logged, preferably both at the diagnostic facility and at the remote service provider.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A method for providing service data to medical diagnostic systems, the method comprising the steps of:
   (a) generating a diagnostic system service request for a designated diagnostic system coupled to an internal network of a medical diagnostic facility;
   (b) transmitting the request to a remote service provider over an external network via a data communication control system coupled to a plurality of diagnostic systems over the internal network;
   (c) receiving and processing the request at the remote service provider;
   (d) transmitting a response from the remote service provider in response to the request.

2. The method of claim 1, wherein the response is transmitted to the data communications control system.

3. The method of claim 1, comprising the further step of transmitting the response to the designated diagnostic system via the internal network.

4. The method of claim 1, wherein the diagnostic system service request is generated at the designated diagnostic system.

5. The method of claim 4, wherein the diagnostic system service request is generated via an interface routine provided on the data communications control system.

6. The method of claim 5, wherein the interface routine includes a web browser application.

7. The method of claim 1, wherein the service request is generated at the data communications control system.

8. The method of claim 1, wherein the service request includes at least data identifying the designated diagnostic system.

9. The method of claim 8, comprising the further step of accessing operational data from the designated diagnostic system in response to the service request.

10. The method of claim 1, wherein the service request is transmitted to the remote service provider via a first data communications medium and the response is transmitted to the medical diagnostic facility via a second data communications medium different from the first medium.

11. The method of claim 10, wherein the first medium includes a wide area network link.

12. The method of claim 10, wherein the second medium includes a satellite link.

13. The method of claim 10, wherein the response is transmitted directly to a diagnostic system.

14. The method of claim 1, comprising the further steps of placing the service request in a queue, and transmitting the service request in accordance with an established schedule.

15. The method of claim 1, wherein the response includes service data for addressing an operational problem of the designated diagnostic system, and wherein the method includes storing the service data for download to the designated diagnostic system.

16. A method for servicing a plurality of medical diagnostic systems, the method comprising the steps of:
   (a) generating a service request for designated diagnostic system of a plurality of diagnostic systems coupled to an internal network of a medical diagnostic facility;
   (b) accessing system data useful in addressing the service request;
   (c) transmitting the service request to a remote service provider via a data communications control system;
   (d) processing the request at the remote service provider; and
   (e) transmitting a service response from the remote service provider to the data communications control system.

17. The method of claim 16, wherein the service request is generated at the designated diagnostic system.

18. The method of claim 16, wherein the system data is stored at the diagnostic system.

19. The method of claim 18, wherein the system data is accessed by the data communications control system and transmitted to the remote service provider.

20. The method of claim 19, wherein the system data is transmitted with the service request.

21. The method of claim 19, wherein the system data is transmitted after the service request and in response to a prompt from the remote service provider.

22. The method of claim 16, wherein the service request and the response are transmitted via different data communications media.

23. The method of claim 16, comprising the further step of forwarding the response to the designated diagnostic system via the internal network.

24. The method of claim 16, wherein the diagnostic systems include at least two imaging systems of different modalities.

25. A system for providing remote service to a plurality of networked medical diagnostic systems, the system comprising:
   a plurality of medical diagnostic systems coupled to an internal network of a medical diagnostic facility, including designated diagnostic system;
   a service request generating circuit for formulating a service request for addressing an operation of the designated diagnostic system; and
   a data communications control system coupled to the internal network and to an external network for transmitting the service request to a remote service provider and for receiving a response to the request from the remote service provider.

26. The system of claim 25, including a remote service provider, the remote service provider receiving the service request, generating the response, and transmitting the response to the data communications control system.

27. The system of claim 26, wherein the control system includes an external network interface for receiving the response via at least two different data communications media.

28. The system of claim 25, wherein the service request is generated at the designated diagnostic system.

29. The system of claim 25, wherein the diagnostic systems include at least two imaging systems of different modalities, and wherein the designated diagnostic system is selected from the at least two imaging systems.

30. The system of claim 25, wherein the operational data useful in responding to the service request is stored at the designated diagnostic system.

31. The system of claim 30, wherein the data communications control system accesses the operational data from the designated diagnostic system via the internal network.

32. The system of claim 25, wherein the data communications control system includes an operator interface, and wherein the service request is generated via the operator interface.

* * * * *